United States Patent [19]

Kimura et al.

[11] 4,080,370
[45] Mar. 21, 1978

[54] PROCESS FOR PRODUCING HIGH PURITY METHOXYANTHRAQUINONES

[75] Inventors: Yoshio Kimura; Yasuhito Goto; Kenzo Ban, all of Kitakyushu; Kiyotomi Kosai, Oaza-Nakami; Haruki Uchida; Kiyoharu Urakawa, both of Kitakyushu, all of Japan

[73] Assignee: Mitsubishi Chemical Industries, Ltd., Tokyo, Japan

[21] Appl. No.: 775,312

[22] Filed: Mar. 7, 1977

Related U.S. Application Data

[63] Continuation of Ser. No. 657,696, Feb. 12, 1976, abandoned.

[30] Foreign Application Priority Data

Feb. 20, 1975 Japan .................................. 50-21137

[51] Int. Cl.$^2$ ............................................. C07C 49/68

[52] U.S. Cl. ................................................... 260/383
[58] Field of Search ...................................... 260/383

[56] References Cited

U.S. PATENT DOCUMENTS 3,892,784   7/1975   Elser et al. .......................... 260/383

*Primary Examiner*—Paul F. Shaver
*Attorney, Agent, or Firm*—Oblon, Fisher, Spivak, McClelland & Maier

[57] ABSTRACT

Methoxyanthraquinones are produced from the corresponding nitroanthraquinones by reacting a nitroanthraquinone with methanol and an alkali in a reaction medium chiefly comprising methanol at a temperature of 50°–130° C under atmospheric or superatmospheric pressure in the presence of molecular oxygen wherein the dissolved oxygen concentration of the reaction medium is maintained at a value of at least 1 ppm.

9 Claims, No Drawings

PROCESS FOR PRODUCING HIGH PURITY METHOXYANTHRAQUINONES

This is a continuation, of application Ser. No. 657,696, filed Feb. 12, 1976, now abandoned.

BACKGROUND OF THE INVENTION

1. Field of the Invention

The present invention relates to a process for producing high purity methoxyanthraquinones. More particularly, the invention relates to an improvement in the process for producing methoxyanthraquinones by reacting nitroanthraquinones with a methanol-alkali mixture.

2. Description of the Prior Art

The production of methoxyanthraquinones from nitroanthraquinones as a starting material is well known as disclosed, for instance, in German Pat. No. 77,818. This disclosure shows a process in which a mixture of dinitroanthraquinones, obtained by dinitrating anthraquinones with a mixed acid solution of concentrated sulfuric acid and nitric acid, is reacted with an alkali metal or an alkaline earth metal hydroxide in a methanolic solution. However, as mentioned in German Offenlegungsschrift No. 2,152,991 (Japanese Patent Provisional Publication No. 51017/1973), this particular process produces about 30–40% by weight of by-products such as diamino-, aminomethoxy-, hydroxymethoxy-, dihydroxy- and aminoanthraquinones. The disclosure of the German Offenlegungsschrift, in turn, also discloses a process for producing 1,5- or 1,8-dimethoxyanthraquinone by heating 1,5- or 1,8-dinitroanthraquinone with potassium hydroxide in methanol. Even when the reaction is conducted in this manner, it is still difficult to control the side reactions which occur and consequently, dimethoxyanthraquinones are produced which contain 10–20% by weight of by-products.

In another prior art approach to the reaction, German Offenlegungsschrift No. 2,314,696 (Japanese Patent Provisional Publication No. 126660/1974) discloses the production of a α-methoxyanthraquinones using potassium carbonate anhydride as the alkali agent. An example of the patent publication shows that the nitrogen content in the α-methoxyanthraquinones produced is less than 0.5%, which is equivalent to about 10% of by-products, calculated on the assumption that the nitrogen comes from the main by-product, aminomethoxyanthraquinone.

A need therefore, continues to exist for a method by which methoxyanthraquinones can be produced from nitroanthraquinones containing substantially reduced amounts of by-products.

In the extensive research which has led to the present discovery, it has been found that the presence of dissolved oxygen in the reaction mixture has a substantial influence on the side reactions which occur, and that when the reaction is conducted in the absence of dissolved oxygen, a large amount of by-products are produced.

SUMMARY OF THE INVENTION

Accordingly, one object of the present invention is to provide a process for producing methoxyanthraquinones from nitroanthraquinones in a manner which substantially reduces the amount of by-products formed in the reaction.

Briefly, this object and other objects of the present invention as hereinafter will become more readily apparent can be attained by a process for producing methoxyanthraquinones from nitroanthraquinones by reacting a nitroanthraquinone with methanol and an alkali in a reaction medium, chiefly comprising methanol at a temperature of 50°–130° C under atmospheric or superatmospheric pressure in the presence of molecular oxygen wherein the dissolved oxygen concentration of the reaction medium is maintained at a value of at least 1 ppm.

DETAILED DESCRIPTION OF THE PREFERRED EMBODIMENTS

Any nitroanthraquinone compound can be used as a starting material in the present invention which reacts under the described conditions to form the corresponding methoxyanthraquinone. Suitable nitroanthraquinones include α-nitroanthraquinones such as 1-nitroanthraquinone, 1,5-dinitroanthraquinone, 1,8-dinitroanthraquinone and mixtures thereof, as well as substituted nitroanthraquinones in which one or more hydrogen atoms of the anthraquinone nucleus are further substituted with halogen, alkyl groups and the like. For example, a mixture of 1,5- and 1,8-dinitroanthraquinones is obtained by nitrating an anthraquinone starting material with a mixed acid or with concentrated nitric acid. The nitroanthraquinone product mixture contains both 1,5- and 1,8-dinitroanthraquinones which can be separated by taking advantage of their solubility differences in a medium such as concentrated sulfuric acid, concentrated nitric acid or an organic solvent such as nitrobenzene. 1-Nitroanthraquinone. can be obtained in a similar manner. Substituted nitroanthraquinones are also obtainable from substituted anthraquinones such as methylanthraquinone, chloroanthraquinone or the like, in a similar manner.

In the reaction of the present invention, molecular oxygen is supplied to the reaction medium such that the concentration of dissolved oxygen is at least 1 ppm. The method by which molecular oxygen is supplied to the reaction medium is not critical and the only requirement is that sufficient oxygen be supplied to the reaction mixture. Molecular oxygen can be supplied to the reaction medium by:

(1) Continuously or intermittently introducing gaseous molecular oxygen or an oxygen containing gas into the reaction mixture. In this embodiment, the gas may either be bubbled into the liquid reaction medium below the surface thereof or it can be introduced by way of an exterior circulating line, if the reactor is provided with such a line;

(2) Dissolving the oxygen in the reaction mixture by pressurizing the reaction system with oxygen or an oxygen containing gas;

(3) Forcing the oxygen to be absorbed into the reaction mixture by continuously or intermittently charging gaseous molecular oxygen or an oxygen containing gas into the gas phase of the reactor and agitating the system by mechanical means such as by stirring, shaking or inverting the reactor. If the reactor is equipped with an exterior circulating line, oxygen may be absorbed into the reaction medium by ejecting the reaction mixture from the inlet of the circulating liquid in the form of a jet stream; or (4) Mixing oxygen or an oxygen containing gas with the starting material or with methanol if the reactor is provided with a recycle system.

Any of the above methods for introducing oxygen into the system can be employed alone or in combination. Furthermore, it will be readily apparent to the skilled artisan that other methods of introducing oxygen into the reaction system can be equally employed as well to achieve the same effect.

Though the mechanistic role of oxygen in the reaction of the present invention has not been clarified, it has been found that some amount of oxygen is consumed in the reaction. The amount of oxygen consumed ranges from about 0.01 to 0.1 mole per mole of nitro group of the nitroanthraquinone, depending on the reaction conditions, i.e., the ratio of reactants, e.g., nitroanthraquinone and methanol; the kind and concentration of alkali; the reaction temperature; and the like. Therefore, the amount of oxygen supplied to the system should be more than the amount consumed in the reaction. For this purpose, oxygen or an oxygen containing gas should be supplied in such a manner that the dissolved oxygen is methanol in the reaction mixture is maintained at a level not less than 0.0001% by weight (1 ppm), preferably 0.0004% by weight (4 ppm) or more. For example, if the first embodiment described above is used to introduce an oxygen containing gas into the reaction mixture, it is preferred to use an amount of gas containing 4 to 20 times the among of oxygen consumed in the reaction. The introduction of oxygen containing gas is continued until the reaction is complete. If the second embodiment above is used, the reaction can be conducted by charging the gas containing oxygen under pressure in an amount containing from 1.5 to 8 times the amount of oxygen consumed in the reaction, and then sealing the system and commencing the reaction or by maintaining a constant pressure of an oxygen containing gas over the system having the same excess oxygen content described. If the third embodiment is used to introduce oxygen in which the oxygen is forced into the system and absorbed under normal pressure, it is preferred to use an oxygen containing gas containing oxygen in an amount of 5 to 25 times the amount of oxygen consumed in the reaction and to continuously introduce the gas into the gas phase of the reaction system until the reaction is complete. In any of the embodiments mentioned above, greater amounts of oxygen can be supplied without any detrimental effects, although no further improvements in the reaction can be expected.

Oxygen can be supplied to the reaction zone as pure oxygen or in the form of an oxygen-containing gas. The term "oxygen containing gas" means a mixture of gaseous molecular oxygen and an inert gas which does not adversely affect the methoxylation reaction. Suitable examples of inert gases include the noble gases such as helium, neon and argon, nitrogen and carbon dioxide. Nitrogen is preferably used because of its commercial advantages. Since the necessary amount of oxygen supplied to the reaction is not extremely large, the concentration of the oxygen in the oxygen containing gas can be as low as several volume percent. The upper limit of the oxygen concentration in the oxygen containing gas should be about several ten percent such as 30 volume percent, from the standpoint of avoiding explosions and economy. Consequently, very convenient and commercially advantageous oxygen containing gases are air and air diluted with nitrogen.

Suitable alkalis used in the process of the present invention include the hydroxides, methylates, carbonates, bicarbonates and acetates of alkali metals. Specific examples of these bases include sodium hydroxide, potassium hydroxide, sodium methylate, potassium methylate, sodium carbonate, potassium carbonate, sodium bicarbonate, potassium bicarbonate, sodium acetate and potassium acetate. Sodium hydroxide is the most advantageous from an economic point of view. The concentration of alkali in methanol reaction solvent is generally in the range of 0.3 - 2.0 mole/l methanol, preferably 0.5 - 1.5 mole/l methanol. Preferably, the alkali concentration is maintained at these concentration levels by adding additional amounts of alkali during the reaction. In the reaction medium of the process of the present invention, it is advantageous to use excess amounts of methanol as both a starting material and a solvent medium in amounts of 400 - 1000 parts by weight per 100 parts by weight of nitroanthraquinone. In order to accelerate the rate of reaction, it is sometimes useful to employ a cosolvent selected from such dipolar organic solvents as N-alkylpyrrolidone, e.g., N-methylpyrrolidone, dimethylsulfoxide and hexamethylphosphoric triamide in amounts of up to about 10% based on the methanol. Although it is not necessary to eliminate the water present in the methanol, the water content should be as low as possible because it decreases the solubility of the oxygen and slows the reaction rate.

The process of the present invention can be conducted either under atmospheric pressure or under superatmospheric pressure. When the reaction is conducted under superatmospheric pressure, pressures of several tens of atms, for example up to 50 $kg/cm^2$ are preferably employed. The reaction temperature under atmospheric pressure varies with the range of 50°–130°C preferably 55°–65° C, and under superatmospheric pressure, 60°–100° C is preferred. The reaction temperature should be selected so that the reaction medium is maintained in the liquid state.

Both the yield and purity of the product methoxyanthraquinones are improved by the present process in comparison to any of the conventional processes. Furthermore, another important feature of the present invention is that the process of this invention does not require the use of expensive alkalis such as potassium hydroxide or potassium bicarbonate, which are necessary in the conventional processes. In other words, when the present invention is employed, high purity methoxyanthraquinones are obtainable in greater yield by means of easily available and less expensive alkalis such as sodium hydroxide.

Methoxyanthraquinones are valuable intermediates for dyestuff production, and blue anthraquinone dyestuffs suitable for dyeing polyester fibers are obtained by successive nitration, hydrolysis, reduction and bromination by methods well known in the art. Furthermore, the dyestuffs eventually obtained from the present process have the additional advantage over the dyestuffs obtained from anthraquinone-α-sulfuric acid formed over a mercury catalyst in that there are no environmental mercury pollution problems which is a problem with the conventional method using the mercury catalyst.

Having generally described this invention, a further understanding can be obtained by reference to certain specific examples which are provided herein for purposes of illustration only and are not intended to be limiting unless otherwise specified.

In the examples, the term "parts" signifies "parts by weight", although as to the gas volume and the capacity of the reactor, "parts by volume" is used. Further, the relationship between "parts by volume" and "parts by weight" is the same as the relationship between the milliliter and the gram. For instance, in Example 1, "600 parts of methanol and 500 parts by volume of air" means that 500 ml of air is used per 600 g of methanol. The gas volume values are expressed under the standard conditions of 0° C and 1 atm pressure. Analysis of the anthraquinones was accomplished by means of high speed liquid chromatography.

The amount of dissolved oxygen in the reaction media was determined in the following manner:

1. The actual amount of the dissolved oxygen was measured in an alkali/methanol solution containing a certain amount of oxygen.

2. A Dissolved Oxygen Analyzer was employed to measure the oxygen content of the same solution.

3. The relationship between the actual amount obtained in step 1 and the value obtained in step 2 was determined. 4. The actual amount of the dissolved oxygen in the reaction medium of each example was calculated from an indicated value based on the above relationship steps 1-3.

The details of each step are as follows:

1. Into a NaOH solution in methanol having an alkali concentration of 0.9 mole/l was bubbled air at 62° C under atmospheric pressure to give a solution saturated with air. A portion of the solution was selected for the determination of the amount of dissolved oxygen. The sample solution selected was placed in a 50 ml volumetric flask and nitrogen was passed through the solution to drive away the dissolved oxygen. The oxygen entrained in the nitrogen was absorbed in a buffer solution (ammonia water containing ammonium chloride). The buffer solution containing the absorbed oxygen was then passed through a 10 meter-long copper pipe, thereby allowing the oxygen to react with the copper of the tube. The solution exiting the tube containing a cuprous salt. One drop of 3% $H_2O_2$ was added to the eluted solution to oxidize the cuprous salt to the corresponding cupric salt. The chemical reactions involved in this sequence are as follows:

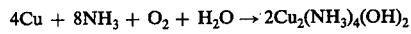

$4Cu + 8NH_3 + O_2 + H_2O \rightarrow 2Cu_2(NH_3)_4(OH)_2$

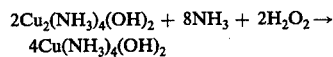

$2Cu_2(NH_3)_4(OH)_2 + 8NH_3 + 2H_2O_2 \rightarrow 4Cu(NH_3)_4(OH)_2$

The blue coloration due to the formation of the cupric salt was measured at a wavelength of 580 nm in a colorimeter. From the results thus obtained, the actual amount of the dissolved oxygen in the airsaturated solution was found to be 0.0020% by weight (20 ppm).

2. Using a Fieldlab Dissolved Oxygen Analyzer manufactured by the Toshiba Beckman Company and a Dissolved Oxygen Analyzer type DO-1A manufactured by Toa Dempa Kogyo Company, the dissolved oxygen content was measured on the same solution as used in step 1 to obtain an indicated value of 8%.

3. The relationship between the actual amount of the dissolved oxygen determined in step 1 and the indicated value by the Analyzer of step 2 was established to be that an indication of 0.4% is equivalent to an actual amount of dissolved oxygen of 1 ppm.

4. In each example, the indicated value of the dissolved oxygen was periodically determined, i.e., the reaction conditions including the flow rate of the oxygen containing gas were controlled according to the indication of the Dissolved Oxygen Analyzer. In order to stabilize the operation, the flow rate or the pressure of the oxygen containing gas was established in such a way that an indication of 1.5% or more was maintained, although the side reaction was generally inhibited at an indication of 0.4% (or 1 ppm of dissolved oxygen).

EXAMPLE 1

27 parts of sodium hydroxide were dissolved in 600 parts of methanol and 100 parts of 1,5-dinitroanthraquinone (consisting of 93.5% 1,5-isomer, 4.5% 1,8-isomer and 2.0% other material) to form a homogeneous slurry. The slurry was stirred and heated to 62° C while bubbling air into the liquid reaction medium at a rate of 500 parts by volume per hour under atmospheric pressure. At this temperature, the reaction was continued for 35 hours and the concentration of the dissolved oxygen was maintained at 13-20 ppm. During the reaction, a solution of 26.8 parts of sodium hydroxide in 100 parts of methanol was further added dropwise over a period of 30 hours immediately after the temperature rise. Bubbling of air was terminated after the reaction was complete. The mixture was allowed to cool to room temperature, filtered, washed and dried to give 84.5 parts of the methoxylated product.

Analysis: 1,5-isomer 94.7%; 1,8-isomer 3.7%; other dimethoxyanthraquinones 1.5%; hydroxymethoxy anthraquinones 0.1%.

For comparison, the same procedure was repeated except that the reaction system was in contact with the open air under atmospheric pressure via a condenser without the positive addition of air. By this technique, 74.6 parts of product were obtained.

Analysis: 1,5-isomer 87.9%; 1,8-isomer 2.9%; other dimethoxyanthraquinones 1.0%; by-products 8.2%.

EXAMPLE 2

The procedure of Example 1 was repeated, using 1000 parts by volume of an oxygen containing gas consisting of 10% oxygen and 90% nitrogen per hour instead of 500 parts of air per hour. The reaction yielded 84.7 parts of the methoxylated product. During the reaction, the concentration of the dissolved oxygen was maintained at 5 – 10 ppm.

Analysis: 1,5-isomer 94.5%; 1,8-isomer 3.6%; other dimethoxyanthraquinones 1.7%; hydroxymethoxyanthraquinones 0.2%.

EXAMPLE 3

45 Parts of sodium hydroxide were dissolved in 600 parts of methanol and 100 parts of 1,5-dinitroanthraquinone (the compoistion being the same as in Example 1) to form a homogeneous slurry. The reaction was continued with stirring at 62° C under atmospheric pressure for 40 hours while bubbling air into the medium at a rate of 1200 parts by volume per hour. The concentration of the dissolved oxygen was 15-20 ppm. Upon completion of the reaction, the reaction mixture was treated as in Example 1 to give 84.0 parts of the methoxylated product.

Analysis: 1,5-isomer 95%; 1,8-isomer 3.2%; other dimethoxyanthraquinones 1.5%; hydroxymethoxyanthraquinones 0.3%.

EXAMPLE 4

32.6 Parts of potassium hydroxide was dissolved in 600 parts of methanol and 100 parts of 1,5-dinitroanthraquinone (the composition being the same as in Example 1) was added to form a homogeneous slurry. The reaction was continued with stirring at 62° C for 35 hours while air was bubbled through the medium at a rate of 500 parts by volume per hour. During the reaction, a solution of 37.5 parts of potassium hydroxide in 100 parts of methanol was added dropwise over a period of 32 hours. The concentration of the dissolved oxygen was 14–20 ppm.

After the reaction, the reaction mixture was treated as in Example 1 to give 85.0 parts of the methoxylated product.

Analysis: 1,5-isomer 94.3%; 1,8-isomer 4.0%; other dimethoxyanthraquinones 1.6%; hydroxymethoxyanthraquinones 0.1%.

For comparison, the same procedure was repeated except that the reaction system was in contact with the open air under atmospheric pressure via a condenser without the positive addition of air to give 81.0 parts of the methoxylated product.

Analysis: 1,5-isomer 91.6%; 1,8-isomer 3.4%; other dimethoxyanthraquinones 1.4%; by-products 3.6%.

EXAMPLE 5

21 Parts of sodium hydroxide were dissolved in 600 parts of methanol and 100 parts of a dinitroanthraquinone mixture containing 1,8-dinitroanthraquinone as the main component (composition: 1,8-form 64.2%; 1,5-form 22.1%; other dinitroanthraquinones 13.7%) were added to form a homogeneous slurry. The slurry was heated to 60° C with stirring and the reaction was continued at the same temperature for 24 hours while maintaining the concentration of the dissolved oxygen at 10–18 ppm by bubbling air into the medium at a rate of 750 parts by volume per hour. During the reaction, a solution of 26.8 parts of sodium hydroxide in 100 parts of methanol was added in portions over a period of 20 hours. After the reaction, the reaction mixture was allowed to cool to room temperature and filtered. The filtered product was washed and dried to give 82.3 parts of the methoxylated product.

Analysis: 1,8-isomer 65.9%; 1,5-isomer 24.5%; other dimethoxyanthraquinones 9.3%; hydroxymethoxyanthraquinone, 0.3%.

EXAMPLE 6

The procedure of Example 5 was repeated except that an oxygen containing gas consisting of 10% oxygen and 90% nitrogen was bubbled into the reaction medium at a rate of 1600 parts by volume per hour to give 82.5 parts of the methoxylated product. During the reaction, the concentration of the dissolved oxygen was maintained at 6 -10 ppm.

Analysis: 1,8-isomer 65.7%; 1,5-isomer 24.3%; other dimethoxyanthraquinones 9.8%; hydroxymethoxyanthraquinones 0.2%.

EXAMPLE 7

30 Parts of sodium hydroxide were dissolved in 600 parts of methanol and 100 parts of 1-nitroanthraquinone (98.0% purity) was added to form a homogeneous slurry. The slurry was heated to 60° C with stirring and the reaction was continued at the same temperature for 20 hours while bubbling air into the reaction medium at a rate of 400 parts by volume per hour. During the reaction the concentration of the dissolved oxygen was 10 - 20 ppm. After the reaction, the addition of air was ceased and the reaction mixture was allowed to cool to room temperature and filtered. The product attained was washed and dried to give 87.5 parts of 1-methoxyanthraquinone (98.8% purity).

EXAMPLE 8

Into an autoclave having a capacity of 1200 parts by volume were charged 480 parts of methanol and 21.6 parts of sodium hydroxide, followed by 100 parts of 1,5-dinitroanthraquinone (the composition being the same as that used in Example 1) to form a homogeneous slurry. The reactor was then pressurized with air to 20 kg/cm$^2$ at room temperature and heated to 70° C, at which temperature and pressure the reaction was continued for 24 hours. During the reaction, a solution of 26.8 parts of sodium hydroxide in 100 parts of methanol was added constantly under pressure over a period of 20 hours starting immediately after the reaction temperature was attained. After the reaction was complete, the system was allowed to cool to room temperature and the pressure was released. The concentration of the dissolved oxygen after the reaction was 20 ppm. The reaction mixture was then treated according to the procedure of Example 1 to give 84.3 parts of the methoxylated product.

Analysis: 1,5-isomer 94.4%, 1,8-isomer 3.5%; other dimethoxyanthraquinones 1.5%; hydroxymethoxyanthraquinone 0.6%.

EXAMPLE 9

Into an autoclave having a capacity of 1200 parts by volume were charged 480 parts of methanol and 14.4 parts of sodium hydroxide, followed by 100 parts of dinitroanthraquinone mixture containing 1,8-dinitroanthraquinone as the main component (the composition being the same as in Example 5) to form a homogeneous slurry. The reactor was then pressurized with air to 20 kg/cm$^2$ at room temperature and heated to 70° C. The reaction was continued for 20 hours. During the reaction, a solution of 26.8 parts of sodium hydroxide in 100 parts of methanol was added constantly under pressure over a period of 16 hours from a time immediately after the temperature rise. After the reaction was complete, the system was allowed to cool to room temperature and the pressure was released. The concentration of the dissolved oxygen after the reaction was 20 ppm. The reaction mixture was then treated according to the procedure of Example 5 to give 83.1 parts of the methoxylated product.

Analysis: 1,8-isomer 65.6%; 1,5-isomer 23.9%; other dimethoxyanthraquinones 10.0%; hydroxymethoxyanthraquinones 0.5%.

EXAMPLE 10

37 Parts of sodium methylate were dissolved in 600 parts of methanol and 100 parts of 1,5-dinitroanthraquinone (the composition being the same as in Example 1) were added to form a homogeneous slurry. The slurry was heated to 62° C with stirring while an oxygen containing gas consisting of 10% oxygen and 90% nitrogen was bubbled into the reaction medium at a rate of 1000 parts by volume per hour. The reaction was continued at the same temperature for 35 hours. During the reaction, a solution of 36.2 parts of sodium methylate in 100 parts of methanol was further added dropwise over a period of 30 hours from a time immediately after the temperature rise. The concentration of the dissolved oxygen during the reaction was 5 - 10 ppm. After the reaction, the reaction mixture was treated as described in Example 1 to give 84.5 parts of the methoxylated product.

Analysis: 1,5-isomer 94.8%; 1,8-isomer 3.7%; other dimethoxyanthraquinones 1.5%.

EXAMPLE 11

40.8 Parts of potassium methylate were dissolved in 600 parts of methanol and 100 parts of 1,5-dinitroanthraquinone (the composition being the same as in Example 1) were added to form a homogeneous slurry. The reaction was continued at 62° C under atmospheric pressure for 35 hours while bubbling an oxygen containing gas consisting of 10% oxygen and 90% nitrogen at a rate of 1000 parts by volume per hour into the reaction medium. During the reaction, a solution of 46.9 parts of potassium methylate in 100 parts of methanol was added dropwise over a period of 30 hours from a time immediately after the temperature rise. The concentration of the dissolved oxygen during the reaction was 6 - 10 ppm. After the reaction, the reaction mixture was treated as in Example 1 to give 85.0 parts of the methoxylated product.

Analysis: 1,5-isomer 94.4%; 1,8-isomer 4.0%; other dimethoxyanthraquinones 0.8%.

EXAMPLE 12

27 Parts of sodium hydroxide were dissolved in a mixture of 570 parts of methanol and 30 parts of N-methyl-2-pyrrolidone and 100 parts of 1,5-dinitroanthraquinone (the composition being the same as in Example 1) were added to form a homogeneous slurry. The slurry was heated to 62° C with stirring under atmospheric pressure while bubbling air at a rate of 700 parts by volume per hour into the reaction medium. The reaction was continued at the same temperature for 25 hours. During the reaction, a solution of 26.8 parts of sodium hydroxide in 100 parts of methanol was added dropwise over a period of 20 hours from a time immediately after the temperature rise. The concentration of the dissolved oxygen during the reaction was 18-23 ppm. After the reaction, the reaction mixture was treated as described in Example 1 to give 83.5 parts of the methoxylated product.

Analysis: 1,5-isomer 96.7%; 1,8-isomer 2.5%; other dimethoxyanthraquinones 0.8%.

EXAMPLE 13

The procedure of Example 12 was repeated using 30 parts of dimethylsulfoxide instead of 30 parts of N-methyl-2-pyrrolidone to give 84.0 parts of the methoxylated product. During the reaction, the concentration of the dissolved oxygen was 18 - 24 ppm.

Analysis: 1,5-isomer 95.2%; 1,8-isomer 3.4%; other dimethoxyanthraquinones 1.2%; hydroxymethoxyanthraquinones 0.2%.

EXAMPLE 14

The procedure of Example 12 was repeated using 30 parts of hexamethylphosphoric triamide to give 83.2 parts of the methoxylated product. The concentration of the dissolved oxygen was 18 - 23 ppm.

Analysis: 1,5-isomer 96.5%, 1,8-isomer 2.8%; other dimethoxyanthraquinones 0.7%.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for producing methoxyanthraquinones by reacting nitroanthraquinones with methanol and an alkali metal hydroxide in a medium chiefly comprising methanol at a temperature in the range of 50–130° C under atmospheric or superatmospheric pressure, the improvement comprising:

supplying gaseous molecular oxygen to the reaction mixture so as to maintain the concentration of the dissolved oxygen in the reaction medium at a level of at least 4 ppm, whereby methoxyanthraquinone product is obtained in high purity.

2. The process of claim 1, wherein said alkali metal hydroxide is sodium hydroxide.

3. The process of claim 1, wherein said gaseous molecular oxygen is supplied in the form of an oxygen containing gas.

4. The process of claim 3, wherein said oxygen containing gas is air or air diluted with nitrogen.

5. The process of claim 1, wherein the reaction medium is methanol.

6. The process of claim 1, wherein the reaction medium comprises methanol and a dipolar organic solvent used in an amount of up to about 10% of the methanol.

7. The process of claim 6, wherein said dipolar organic solvent is N-alkylpyrrolidone, dimethylsulfoxide or hexamethylphosphoric triamide.

8. The process of claim 1, wherein 400 to 1000 parts by weight of methanol are combined with 100 parts by weight nitroanthraquinone.

9. The process of claim 1, wherein the concentration of said alkali in methanol ranges from 0.3 to 2.0 mole per liter.

* * * * *